United States Patent [19]

Laukien

[11] 4,022,192
[45] May 10, 1977

[54] APPARATUS FOR MEASURING THE FREQUENCY OF CARDIAC PULSES

[76] Inventor: Günther R. Laukien, c/o Bruker-Physik AG, am Silberstreifen, 7501 Karlsruhe-Forchheim, Germany

[22] Filed: Aug. 4, 1975

[21] Appl. No.: 601,297

Related U.S. Application Data

[63] Continuation-in-part of Ser. No. 516,395, Oct. 21, 1974, abandoned.

[52] U.S. Cl. .................. 128/2.06 F; 128/2.05 T
[51] Int. Cl.² .......................................... A61B 5/04
[58] Field of Search ............... 128/2.05 P, 2.05 R, 128/2.05. T, 2.06 A, 2.06 F, 2.06 R

[56] References Cited

UNITED STATES PATENTS 2,492,617  12/1949  Boland et al. ............ 128/2.06 F
3,575,162   4/1971  Gaarder .................. 128/2.06 A
3,599,628   8/1971  Abbenante et al. ........ 128/2.06 F
3,648,688   3/1972  Ohanlon, Jr. et al. ..... 128/2.06 A
3,699,949  10/1972  Ohanlon, Jr. et al. ..... 128/2.06 A
3,773,038  11/1973  Smith et al. ............ 128/2.06 F
3,807,388   4/1974  Orr et al. .............. 128/2.05 T
3,841,314  10/1974  Page ................... 128/2.05 T Primary Examiner—William E. Kamm
Attorney, Agent, or Firm—Pennie & Edmonds

[57] ABSTRACT

An apparatus is disclosed for examining and analyzing cardiac pulses which is capable of determining instantaneous cardiac pulse frequencies, short and long-time averages of the instantaneous frequencies, drifts in the short and long-time averages, average fluctuations of the instantaneous pulse frequencies about the short-time average value, and the average rate of change of the fluctuations. The instantaneous cardiac pulse frequency may be determined from as few as two successive cardiac pulses.

17 Claims, 9 Drawing Figures

APPARATUS FOR MEASURING THE FREQUENCY OF CARDIAC PULSES

CROSS REFERENCE TO THE PARENT APPLICATION

This application is a continuation-in-part of application 516,395 filed Oct. 21, 1974 and now abandoned.

BACKGROUND OF THE INVENTION

The present invention relates to an apparatus for examining the cardiac pulse frequency. A generally known method of measuring the cardiac pulse frequency consists of measuring the pulse for 1 minute. In order to shorten this relatively long measuring period, the pulse is often measured for a shorter period, e.g. for 15 seconds, with the resulting number then being multiplied by four. However the accuracy of this method is lower than the accuracy of measuring the heartbeats for one whole minute, as fractions of heartbeats cannot be measured. The number of heartbeats measured within a period of fifteen seconds, for example, can be up to almost one heartbeat too high or too low relative to the actual value, which is too large an error for precise examinations.

SUMMARY OF THE INVENTION

An object of the present invention is to permit faster measurement of the frequency of cardiac pulses than possible with the methods described above without excessive error. The present invention comprises a timer for determining the period of time between two or more successive cardiac pulses and means for determining the cardiac pulse frequency from the period so determined. An advantage of the invention is that the measurement requires only a relatively short period. With the timer the period between two successive cardiac pulses can be determined very precisely, and by forming a reciprocal value the frequency can be determined from the period.

Two successive cardiac pulses may be employed for determining the cardiac frequency; however, while largely maintaining the advantage of rapid determination of the cardiac frequency, it is also possible to determine the interval between two cardiac pulses separated by at most only a few intervening cardiac pulses. The total period of time for two or three cardiac pulse periods may be measured and the cardiac frequency calculated therefrom. If the period for fifteen or so successive heartbeats is determined, the measurement time is about fifteen seconds, which is just as long as in previously used methods; the accuracy, however, is much greater.

Since heartbeats themselves cannot be measured directly, appropriate transducers which provide an electrical pulse for every heartbeat are employed. For example, such transducers might respond to pressure fluctuations in an artery.

The invention may include an average-value measuring means for determining the average value of the pulse frequency within a given period of time. An advantage of determining the average pulse frequency is that compensation can be made for short-time fluctuations in the cardiac pulse frequency, resulting in a steadier reading if the average value is indicated by means of a meter or digital display, for example. In addition this average value can also be employed as a comparative value for the instantaneous cardiac frequency or for other average values. It is advantageous to provide a plurality of average-value measuring means, for determining the average values over varying periods of time.

The present invention may include a flutter-value measuring means for determining the difference between the instantaneous cardiac pulse frequency and the short-time average value. Flutter refers to a fluctuation of the instantaneous cardiac pulse frequency about the short-time average value. The absolute values of the differences or alternatively the squares of the differences, can be formed and then averaged to provide a steady reading and to facilitate analysis. If there is no summing or squaring of this type, it is possible for positive or negative differential values to cancel out during averaging with the result that in spite of a flutter in the cardiac pulse frequency, no flutter value is determined.

As will be explained below, the average value with which the instantaneous cardiac frequency is compared for determination of the flutter value is only available at a time later than the instantaneous cardiac pulse frequency. It is therefore advantageous to store the instantaneous cardiac pulse frequency value and to compare it with the average value at a later time. It is also possible to determine a flutter value by comparing the instantaneous cardiac pulse frequency with the average value available at the moment, which corresponds to pulse frequencies at earlier times. In this case, however, it is possible for a slow change of the average value to influence the measurement of the flutter value. To compensate for this effect, the influence of a slow change of the average value of the cardiac pulse frequencies may be taken into account in the flutter value reading. This may be accomplished, for example, by providing both a flutter-value reading determined from the absolute values of the differences between the instantaneous cardiac pulse frequency and the short-time average value and a second reading in which the differences are simply averaged over a given period of time with the proper algebraic signs. Comparison of the two readings indicates whether the flutter-value reading is genuine, or is an artifact simulated by a change of the average cardiac pulse frequency. For example, if there is no flutter, but the instantaneous cardiac pulse frequency is increasing steadily, the second reading will indicate a value which equals the flutter-value measurement. On the other hand, if there is pure flutter and the cardiac pulse frequency average value does not change, the second reading will be zero. When the second reading differs from zero, but is smaller than the flutter-value reading there is both flutter and a change in the average value of the cardiac pulse frequency.

It is also possible with the present invention to measure the flutter value independently of changes in the average value of the cardiac pulse frequency. This can be accomplished by subtracting changes in the average value of the cardiac pulse frequency from the flutter value. This reduces the possibility of an erroneous reading by the flutter-value measuring means.

The present invention may also provide means for indicating a "differential flutter value", which measures the rate of change of the instantaneous cardiac pulse frequency. As with the flutter-value measuring means, it may be advantageous to determine the absolute values of the rate of change. How this differential flutter value is determined will be explained in more detail below.

The present invention may further provide for comparing two cardiac pulse frequency average values determined at different times, thus indicating any drift in the average value. This permits determination of long-term alterations in the cardiac pulse frequency, such as may occur during physical activity. It is possible to determine the drift within periods of differing duration with the present invention, and in addition it is possible to determine the drifts of different average values, i.e., averages taken over periods of differing duration.

The timer of the present invention can be constructed in various ways. For example, it may comprise switching means and a voltage ramp generator which produce a linearly increasing voltage between two successive cardiac pulses. The final voltage is then a measure of the time between the pulses. In an alternate embodiment the timer comprises a counter whose input is connected with the output of a pulse generator by means of a gate which is opened during a predetermined number of cardiac pulse periods, for example, during one period. The pulse generator produces a pulse sequence with a recurrence frequency, denoted $f1$, which is greater than the cardiac pulse frequency. Thus the counter reading, denoted T, achieved after closing the gate is a measure of the duration of the cardiac pulse period and thus also for the cardiac pulse frequency. An advantage of the latter method is that the time to be measured can be determined with high accuracy if frequency $f1$ is sufficiently high. The counter reading T may be read by a digital computer which can calculate the instantaneous cardiac pulse frequencies and the above-described values derived therefrom from the individual counter readings supplied to it quickly and accurately.

An alternate method for determining the cardiac pulse frequency from the pulse period may be accomplished if the input to an adjustable frequency divider whose divisional factor may be set to be 1/T by the counter is connected with the output of an auxiliary pulse generator which supplies a pulse sequence with a recurrence frequency, denoted $f2$, which is larger than $f1$ and the output of the frequency divider is fed to a frequency measuring means.

This arrangement forms the reciprocal value in a simple manner. The pulse sequence with the frequency of $f2$ represents the dividend and the number T is the divisor. The pulse sequence appearing at the output of the adjustable divider has a frequency, denoted $f_T$, which is larger than the cardiac pulse frequency by a factor of $f2/f1$. Thus, the cardiac pulse frequency is multiplied by a given factor greater than one, which provides the advantage that the frequency $f_T$ can be made large enough so that it can be determined to a sufficient degree of accuracy with the usual method of frequency measurements within a short measuring period. The measurement of frequency $f_T$ may be performed by a frequency-measuring means such as described below. It is advantageous for these frequency measuring means to be calibrated in such a manner that they do not indicate the frequency $f_T$ directly, but instead indicate the cardiac pulse frequency corresponding thereto. The frequency measuring means may determine the frequency as a digital value; however it is also possible for it to provide a voltage which is proportional to the frequency $f_T$ and therefore to the cardiac pulse frequency. This voltage can then easily be further processed by analog computing means.

A frequency measuring means suitable for incorporation in the present invention comprises a first integrating network whose input is connected with the output of the adjustable divider and whose output voltage is proportional to the cardiac pulse frequency. Integrating networks of this nature are well known in the art. If desired, the pulses coming from the adjustable divider can be sent through a pulse shaper in order to feed the first integrating network with pulses having a constant time-voltage area. In a preferred design, the time constant, denoted $\tau 1$, of the first integrating network is significantly smaller than the interval between two successive cardiac pulses. This provides the advantage that the voltage at the output of the first integrating network, which measures the instantaneous cardiac pulse frequency, adjusts to its final value very quickly. This is made possible by selecting frequency $f_T$ in such a manner that it is much higher than the cardiac pulse frequency. The time constant $\tau 1$ can be 0.1 second, for example.

To obtain an average value of the cardiac pulse frequency, the input of a second integrating network with an integration time constant denoted $\tau 2$, greater than $\tau 1$, may be coupled with the output of the first integrating network.

The second integrating circuit may be provided with circuitry for reducing its integration time constant when the apparatus is switched on, permitting the second integrating network to adjust itself very rapidly. The integration time constant may then be brought to its normal value $\tau 2$ in order to provide the average value corresponding to this time constant.

The present invention may include a differential amplifier for measuring the flutter-value. When a signal proportional to the instantaneous pulse frequency is supplied to one input of the differential amplifier; for example, an inverting input, and a signal proportional to the average value is supplied to the other input; a noninverting input, the output of the differential amplifier gives a measure of the flutter-value. Such flutter-value measuring means are of conventional design and the two input signals required may readily be produced in the form of voltages. Such signal voltages would ordinarily be available in the circuits for examining the cardiac pulse frequency.

The drift measuring means referred to above may comprise a sample-and-hold circuit for storing a sampled average value of a cardiac pulse frequency and a differential amplifier. The instantaneous average value may be supplied to one input of the differential amplifier and the stored average value supplied to the other input. The drift may then be displayed by indicating means which can be switched to the output of the differential amplifier at predetermined times. If desired the indicating means may include a sample-and-hold circuit for storing the output signal from the differential amplifier. This arrangement is preferred if it is not otherwise possible for the indicating means to continuously store a value supplied thereto.

BRIEF DESCRIPTION OF THE DRAWINGS

These and other objects, features, and elements of the present invention will become more readily apparent from the following detailed description of the accompanying drawings. The features contained in the description and drawings may be employed individually or in any desired combination in other embodiments. In the drawings.

Like reference numerals designate like parts throughout the drawings.

DETAILED DESCRIPTION OF THE DRAWINGS

Figure 1:
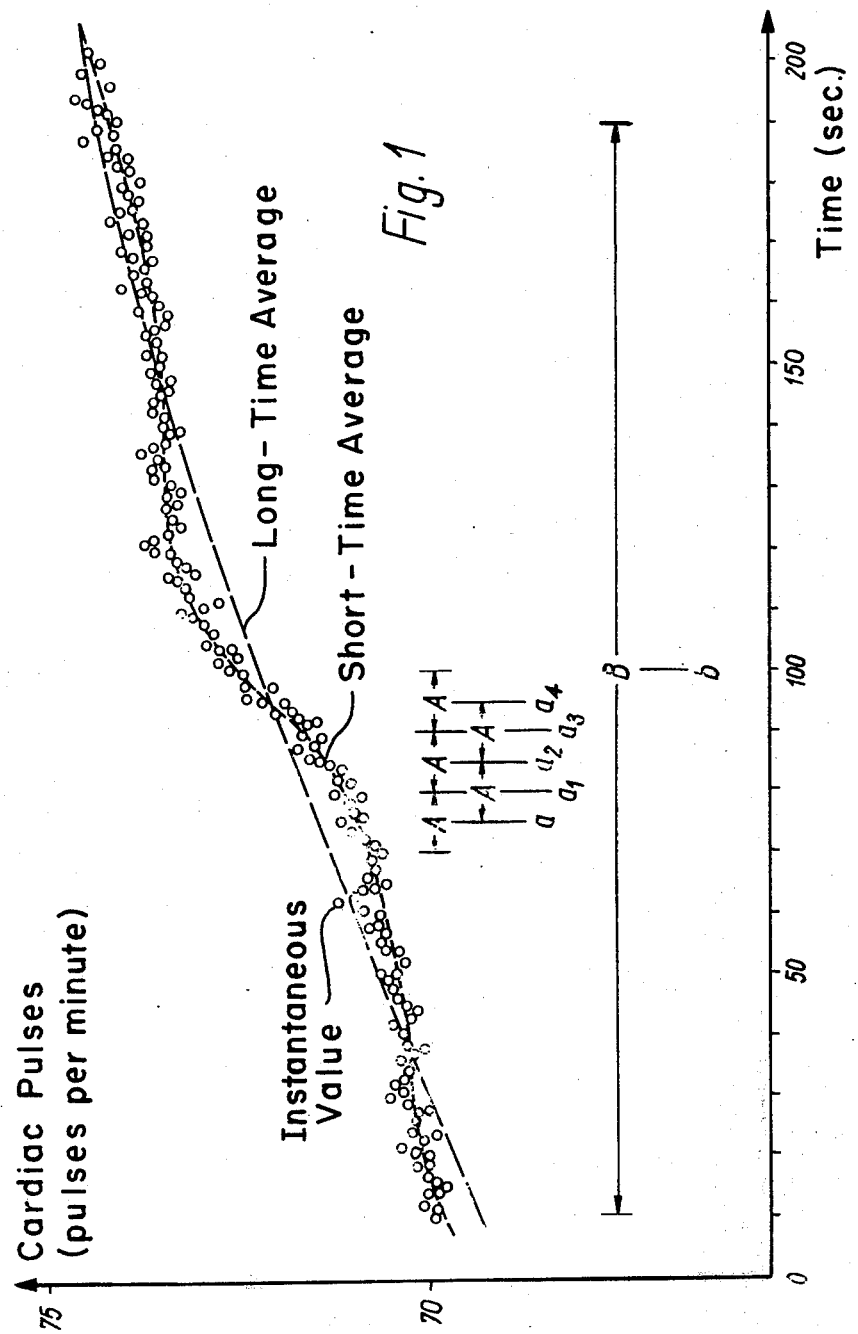
FIG. 1 is a graph characterizing the cardiac pulses of a test subject as a function of time.

Referring now to the drawings, FIG. 1 is the graph, by way of example, of the cardiac pulse frequency of a certain person over a period of time. Individually measured instantaneous values are indicated by small circles. The lowest cardiac pulse frequencies shown in FIG. 1 are about 70 beats per minute, the highest are approximately 75 beats per minute.

The individually measured instantaneous values fluctuate around a short-time average value, and this in turn fluctuates around a long-time average value.

At the present time, there is no recognized nomenclature for the individual characteristic parameters for the curve of the cardiac pulse frequency (cardiac rhythm) as a function of time; the following designations are therefore employed herein:

The "instantaneous value" of the cardiac frequency is that cardiac frequency value which results from the measurement of two successive heart beats; the measuring time therefore is approximately 0.5 to 1 sec., depending upon the cardiac frequency.

The "short-time average value" of the cardiac frequency at a given time can be defined through averaging the approximately 5 to 15 instantaneous value measurements of the cardiac frequency immediately preceding the given time and the approximately 5 to 15 measurements immediately following the cardiac frequency. The short-time average value would thus result from an average of approximately 10 to 30 instantaneous value measurements of the cardiac frequency and the measuring time would therefore be approximately 5 to 30 seconds. As is indicated in FIG. 1, the short-time average value at the time designated $a$ (70 seconds on the time scale) is formed from the average value of the instantaneous values located in a period A of 5 seconds each on either side of time $a$.

The "long-time average value" of the cardiac frequency at a time $b$ can be defined in an analogous manner to the shorttime average value; however in this case the average value is formed from approximately 300 to 1,000 instantaneous value measurements of the cardiac frequency. The measuring time therefore is approximately 3 to 15 minutes.

As is indicated in FIG. 1, for example, the long-time average value of time $b$ (100 seconds on the time scale) results from the instantaneous values occurring within a period B of 90 seconds before and after time $b$.

Thus, both the short-time average value and the long-time average value can only be determined for a given time after a certain period has elapsed subsequent to said time. Thus, for example, if it is desired to compare the instantaneous value of the cardiac frequency at a given time with the short-time average value or the long-time average value of the same moment in time, this comparison can only be performed at a later time when the corresponding average value is available. It is therefore desirable to store the instantaneous value until an average value is available.

If the apparatus for measuring the cardiac frequency includes digital computing means having a memory or storage registers, the instantaneous values may easily be stored in digital form. If the apparatus has analog computing means, the required intermediate storage of values can be handled by sample-and-hold circuits, for example.

The "flutter value" at a given time may be obtained by forming the average value of approximately 5 to 15 of the previous and approximately 5 to 15 of the subsequent measurements of the absolute values of the difference between the instantaneous value and the corresponding short-time average value. Alternatively, instead of the absolute values of the difference, the squares of the fluctuation values can also be employed. Since determination of the short-time average value requires approximately the same amount of time, the measuring time is approximately 10 to 60 seconds. The flutter value is a parameter of the short-time constancy of the cardiac frequency.

As shown in FIG. 1, the respective short-time average values can be determined in various ways. It is possible to determine the short-time average value at times $a$, $a2$, $a4$, etc., so that periods A, which belong to these times, follow one another successively, without interruption. However it is also possible to determine the short-time average values at times $a$, $a1$, $a2$, $a3$, $a4$, etc., with these times being selected in such a manner that the corresponding periods A overlap mutually, e.g. with each period overlapping one half of the preceeding period as shown in FIG. 1. This latter method of determining the short-time average values is preferred because of the finer time mosaic, which is desirable for reliable determination of the flutter value.

The "differential flutter value" also provides a parameter for the short-time constancy of the cardiac frequency and is especially sensitive to rapid changes in cardiac frequency. The differential flutter value describes the speed of change of the instantaneous cardiac pulse frequency. The measuring time amounts to approximately 5 to 30 seconds.

The differential flutter value at a given time can be defined by forming the difference between two successive instantaneous value measurements in one measuring area, extending over approximately 5 to 15 of the preceding and 5 to 15 of the subsequent instantaneous value measurements. The average value of the differential values thus determined is subtracted therefrom, absolute values formed, and the average value of said absolute values then determined, giving the desired differential flutter value. Here, also, the squares can be employed instead of absolute values.

The following mathematical derivation can now be drawn for a better understanding of the differential flutter value.

The instantaneous value $f(t)$ of the cardiac frequency may be approximately represented by a short-time average value $f_o + m\,t$ which changes in a linear manner, upon which the short-time fluctuations $\Delta f(t)$ are superimposed, i.e., $$f(t) = f_o + m\,t + \Delta f(t).$$

To approximate the difference between two successive instantaneousvalue measurements, we view the cardiac frequency $f(t)$ as a continuous curve connecting all measured instantaneous values and form the differential quotient $df(t)/dt$. Employing our expression for $f(t)$, we obtain:

$$\frac{df(t)}{dt} = m + \frac{d[\Delta f(t)]}{dt}$$

The average value for period of time T centered about time $\tau$ is given by:

$$\frac{1}{T}\int_{\tau-\frac{T}{2}}^{\tau+\frac{T}{2}} \frac{df(t)}{dt}\cdot dt = m + \frac{1}{T}\int_{\tau-\frac{T}{2}}^{\tau+\frac{T}{2}} \frac{d[\Delta f(t)]}{dt}\cdot dt$$

$$= m + \frac{1}{T}\left[\Delta f\left(\tau+\frac{T}{2}\right) - \Delta f\left(\tau-\frac{T}{2}\right)\right]$$

$$\approx m.$$

The second term of the sum will tend toward zero for a sufficiently long period of time T, thereby resulting in $$\frac{1}{T}\int_{\tau-\frac{T}{2}}^{\tau+\frac{T}{2}} \frac{df(t)}{dt}\cdot dt = m.$$

The average of the differential quotients of the cardiac frequency is thus identical with the increase of the short-time average value or, as we shall see, with the short-time drift of the cardiac frequency.

The differential quotient of the cardiac frequency minus the drift value $m$ is thus identical with the differential quotients of the short-time fluctuations $\Delta f(t)$ $$\frac{df(t)}{dt} - m = \frac{df(t)}{dt} - \frac{1}{T}\int_{\tau-\frac{T}{2}}^{\tau+\frac{T}{2}} \frac{df(t)}{dt}\cdot dt = \frac{d[\Delta f(t)]}{dt}.$$

We designate the average value of the absolute value of the differential quotient of the short-time fluctuations, measured over period of time T, the differential flutter value. Its value is given by $$\frac{1}{T}\int_{\tau-\frac{T}{2}}^{\tau+\frac{T}{2}} \left|\frac{d[\Delta f(t)]}{dt}\right|\cdot dt\,.$$

The simple flutter value can also be determined from the differential quotients $df(t)/dt$ of the cardiac frequency. This is computed as follows:

1. Determine the differential quotient of the short-time fluctuations $\Delta f(t)$ $$\frac{d[\Delta f(t)]}{dt} = \frac{df(t)}{dt} - \frac{1}{T}\int_{\tau-\frac{T}{2}}^{\tau+\frac{T}{2}} \frac{df(t)}{dt}\cdot dt$$

2. Integrate the differential quotients $$\int^t \frac{d[\Delta f(t)]}{dt}\cdot dt = \Delta f(t) + C,$$

where C is a constant of integration

3. Form the average value of this integral $$\frac{1}{T}\int_{\tau-\frac{T}{2}}^{\tau+\frac{T}{2}}[\Delta f(t) + C]dt = \frac{1}{T}\int_{\tau-\frac{T}{2}}^{\tau+\frac{T}{1}} \Delta f(t)\,dt + C = C$$

4. The integral in (2) minus the average value C in (3) thus provides the short-time fluctuations $\Delta f(t)$ 5. By definition, the average value of the absolute values of the short-time fluctuations thus results in the flutter value:

$$\text{Flutter valve} = \frac{1}{T}\int_{\tau-\frac{T}{2}}^{\tau+\frac{T}{1}} |\Delta f(t)|\,dt$$

The "short-time drift" results from the slope of the short-time average-value curve, cf. FIG. 1. It can be determined by taking the difference between two short-time average values of the cardiac frequency at intervals of about 5 to 30 seconds and dividing this difference by said interval. The short-time drift indicates whether the cardiac frequency, observed for a period of 5 to 30 seconds, is in the process of increasing or decreasing. Its algebraic sign can be either positive or negative.

The "long-time drift" results from the slope of the long-time average-value curve, cf. FIG. 1. It can be determined by taking the difference between two long-time average values of the cardiac frequency at an interval of about 3 to 15 minutes and then dividing this difference by said interval. The long-time drift indicates whether, observed for a period of approximately 3 to 15 minutes, the cardiac frequency has a tendency to increase or decrease. Its algebraic sign can be either positive or negative.

In the above-mentioned definitions, the indicated measuring times and numbers of heartbeats from which the averages are formed are considered only to be guidelines. Deviations can be made from the proposed values, depending upon practical requirements.

Figure 2:
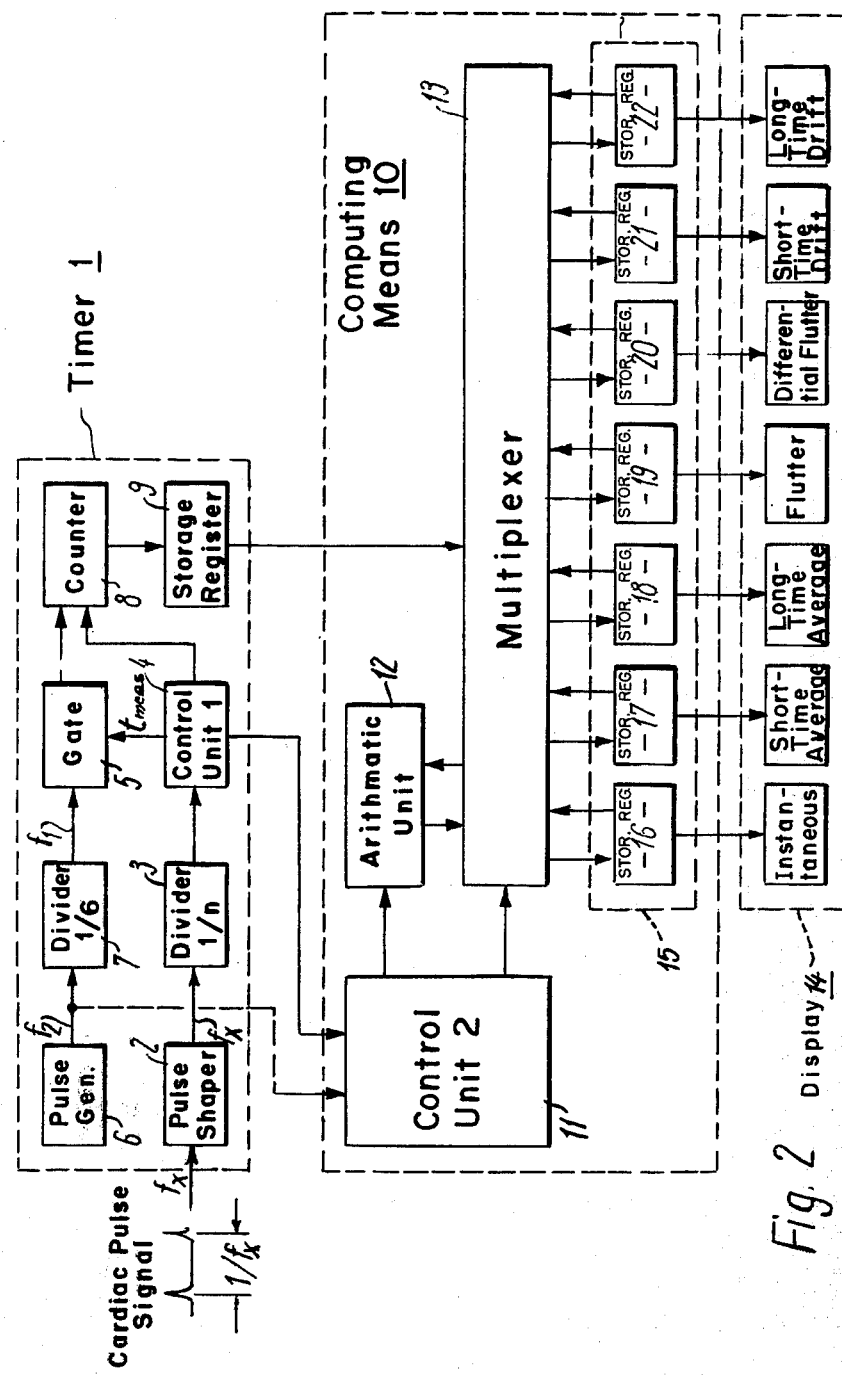
FIG. 2 is a block diagram of a first embodiment of the invention which includes digital computing means.

A first embodiment of the present invention is shown in FIG. 2 in the form of a schematic block diagram. This embodiment includes digital computing means for analyzing the times determined by a timer 1. An electrical cardiac pulse signal of frequency $f_x$, supplied by a suitable probe (not shown), comprises of individual pulses spaced at intervals of $t_x = 1/f_x$. This signal is supplied to the input of a divider means 3 via a pulse shaper 2 which shapes the individual cardiac pulses in a manner which is suitable for further processing. Divider means 3 is employed if the instantaneous value of the cardiac frequency is not to be derived from two successive cardiac pulses, i.e., one single cardiac pulse period, but from a plurality of cardiac pulse periods. Since an object of the invention is to derive instantaneous values of the cardiac frequency, it is assumed below that divider means 3 does not divide the frequency by a large factor. In other words in preferred embodiments of the invention the pulse frequency $f_x/n$ at the output of divider means 3 is of the same magnitude as $f_x$, the pulse recurrence frequency at the input of divider means 3. In what follows it will be assumed that the cardiac pulse frequency is to be derived a single cardiac pulse period so that divider means 3 will be assumed not to alter the pulse frequency, i.e., $n = 1$. From the output of divider means 3 a train of the pulses having the frequency $f_x$ to be measured advances to the input of a first control unit 4, which is connected with the control input of gate 5 and which enables said gate during the period between two successive cardiac pulses. A pulse generator 6 supplies a pulse train with a fixed recurrence frequency $f_2$, which is supplied to the input of a second divider means 7, which converts said pulse train in such a manner that the pulse recurrence frequency $f_1$ appearing at the output of second divider means 7 has a value of $f_2/6$. The output of second divider means 7 is connected to the signal input of gate 5. The signal output of gate 5 is connected to the counting input of a counter 8, which counts the pulses from gate 5 during measuring time $t_{meas} = 1/f_x$. The purpose of the second divider means with a dividing factor of 6 is to alter the time value in such a manner that after formation of the reciprocal value there will be a reading which must only be corrected by a factor of 10 in order to provide a direct reading in heartbeats per minute. The conversion factor of 60 could also be provided directly in the computing means.

One control input of counter 8 is connected with an output of the first control unit 4, which controls counter 8 in such a manner that it transfers its reading, which is a measure of the time $1/f_x$, to an intermediate storage register 9 after gate 5 is disabled.

It is advantageous for timer 1 to be able to measure the times of directly successive periods of the pulse signal from divider means 3. Although means for accomplishing this are not shown in FIG. 1, this result can be achieved, for example, by providing two counters in place of one counter 8, which alternately measure the times of successive periods.

Computing means 10 has a second control unit 11, in which are stored programs for computing the characteristic parameters of cardiac rhythm. Second control unit 11 controls both an arithmetic unit 12, which performs the individual arithmetic operations as well as a multiplexer 13, which routes signals within computing means 10 among arithmetic unit 12 and storage registers making up a storage unit 15 as required for performing individual arithmetic steps and for output of the resultant values at a display 14. Second control unit 11 receives timing signals from timer 1. Both the cardiac pulse signal (solid line from the first control unit 4 to the second control unit 11) as well as the pulse train from pulse generator 6 (dashed line from pulse generator 6 to the second control unit 11) can be employed for the timing signal.

The output of intermediate storage register 9 is connected with multiplexer 13, which calls up the counter readings contained in intermediate storage register 9. Interposed between multiplexer 13 and display 14 is a storage unit 15 having a separate storage registers 16, 17, 18, 19, 20, 21 and 22 for each display provided in this embodiment: instantaneous value, short-time average value, long-time average value, flutter value, differential flutter value, short-time drift and long-time drift.

The individual storage registers provide for both intermediate storage of the values to be indicated by display 14, as well as storage of a plurality of values determined at differing times. For example, an instantaneous value measured at a certain time can be retained in storage unit 15 to be compared later with a short-time average value which could only be determined at a later time. This feature is used, for example, in determining the flutter value, since, as mentioned above, determining the flutter value involves comparing an instantaneous value with the short-time average value corresponding to the same time. In the same manner, short-time average values from different times and long-time average values from different times are stored in storage registers 17 and 18 in order to be available to determine the short-time drift and the long-time drift therefrom.

Figure 3:
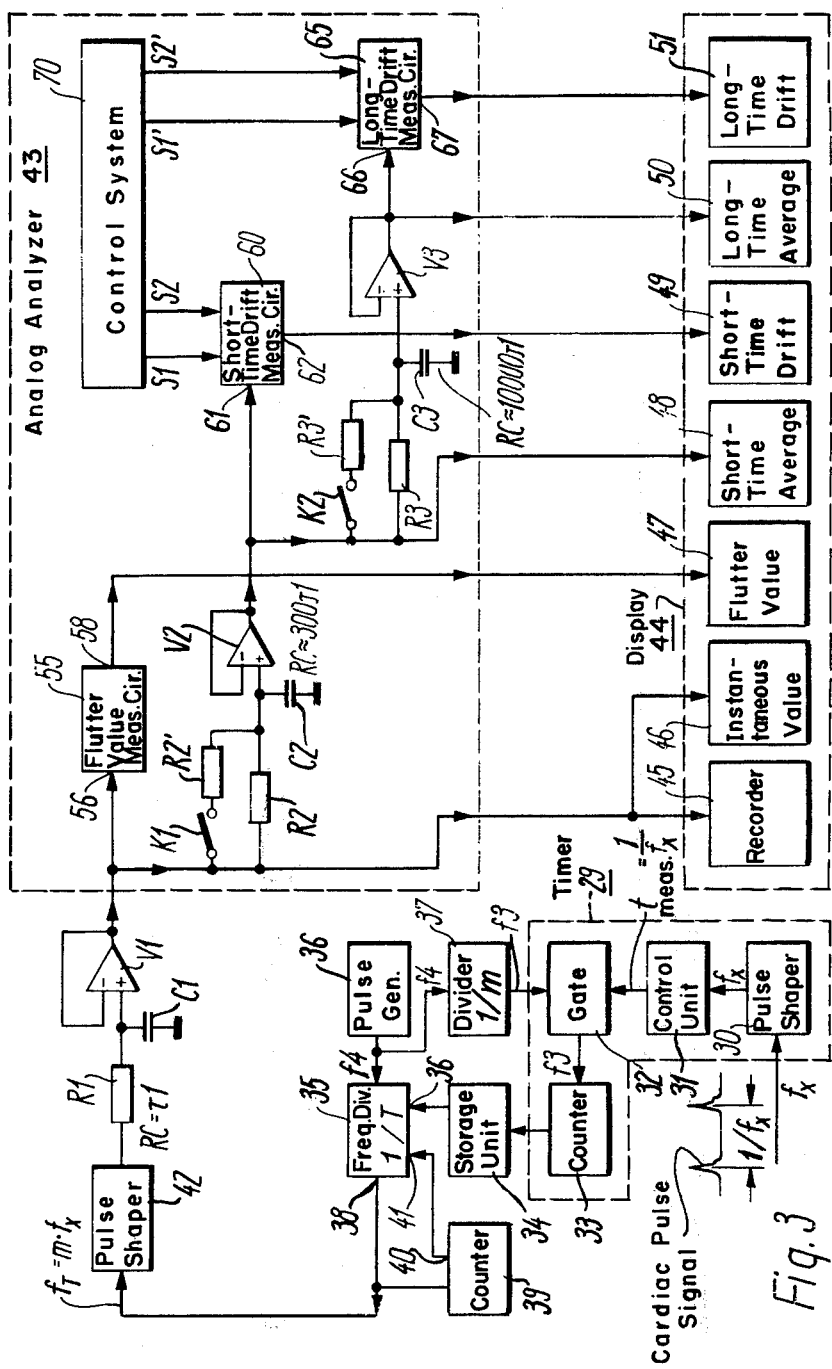
FIG. 3 depicts a second embodiment of the invention which includes analog computing means.

A second embodiment of the invention is shown in FIG. 3, in which analog computing elements are employed. The electrical cardiac signal with the frequency $f_x$ to be measured is supplied to the input of a timer 29 in which, as in the first embodiment, a pulse shaper 30 produces a pulse shape which is suitable for further processing. For example pulse shaper 30 may produce rectangular pulses from jagged pulses at its input. From the output of pulse shaper 30, the pulse train, still with a frequency of $f_x$, advances to the input of a control unit 31, which enables a gate 32 during the measuring time $t_{meas}$, which corresponds to the period $1/f_x$. If desired, in the same manner as in the first embodiment, divider means can be interposed between pulse shaper 30 and control unit 31 in order to permit the time between a plurality of successive periods to be measured.

A pulse train with a frequency of $f3$ is supplied to the signal input of gate 32. When gate 32 is enabled this signal reaches the counting input of a counter 33 from the signal output of gate 32. After disabling gate 32, counter 33 supplies its reading T, which is a measure of the length of the period, to a storage unit 34. The signal input of an adjustable frequency divider 35 whose ratio of division can be set to the value 1/T by the respective number T in storage unit 34, is connected with the output of a pulse generator 36, which supplies a train of pulses with a recurrence frequency of $f4 = 10$ MHz. This pulse train is also supplied to the input of a second divider 37 which, in this embodiment, has a ratio of division of 1/3000 (i.e. $m = 3000$), so that the train of pulses appearing at the output of the second divider 37, and thereafter supplied to the signal input of gate 32, has a recurrence frequency given by $f3 = f4/3000$.

The frequency $f4$ supplied to the signal input of adjustable frequency divider 35 is divided by the factor T, so that a pulse train with a recurrence frequency of $f_T = f4/T$ appears at output 38 of divider 35. Since gate 32 is open during the measuring time $t_{meas} = 1/f_x$, the reading T determined by counter 33, which is characteristic of the duration of the period, has the value $T = f3/f_x$. However since $f3 = f4/m$, this results in $$T = \frac{f4}{m \cdot f_x}.$$

(In this embodiment $m$, the number by which divider 37 divides its input, is 3000.) It follows therefrom that the value of frequency $f_T$ appearing at output 38 of adjustable divider 35 is $m f_x$. The arrangement thus far described therefore provides multiplication of the cardiac frequency $f_x$. This multiplication is performed because frequency $f3$ is smaller than frequency $f4$.

The number $m$, by which divider 37 divides frequency $f4$, may not be selected too high, as the accuracy of the multiplication would then be too low. If, for example, $m = 3000$ and $f4 = 10$ MHz, as is the case in this example, and if a value of $f_x = 1 - 2$ Hz is assumed for the cardiac frequency, the relative accuracy of the multiplication is $$\epsilon_t = \frac{1}{T} = \frac{m f_x}{f4} = 3 \times 10^{-4} - 6 \times 10^{-4},$$

which should generally be sufficient for the present application. The divisional factor $1/m$ of divider 37 is preferably chosen so that the frequency of the signal at the output of the divider is substantially lower than frequency $f4$ but substantially greater than the cardiac pulse frequency $f_x$.

The pulse train appearing at output 38 of adjustable frequency divider 35, has a recurrence frequency given by $f_T = m f_x$ so that cardiac frequencies $f_x$ in the range of from 1 to 2 Hz produce corresponding recurrence frequencies in the range of from 3 to 6 kHz, which can be measured much more easily by common frequency meters than the actual, low cardiac frequency. Since the factor $m$ is known, the cardiac frequency can therefore easily be determined from the reading of a frequency meter attached to output 38 of adjustable divider 35.

The arrangement for measuring the duration of period $1/f_x$, comprising control unit 31, gate 32 and counter 33, may be designed to permit the determination of the respective durations of directly successive cardiac pulse periods.

In order to ensure that the frequency $m f_x$ supplied by adjustable divider 35 is present for precisely the same period as the corresponding cardiac frequency $f_x$, that is for the same duration as the period between the corresponding cardiac pulses, there is an additional counter 39, whose counting input is connected with output 38 of adjustable divider 35 and which has a control output 40 which is connected with a control input 41 of adjustable divider 35. This arrangement only permits alteration of the division factor of adjustable divider 35 when it has strobed out a prescribed number of pulses, which in this case is set to be exactly m pulses. For example, two successive heartbeats separated by 1 second represent a frequency of $f_x = 1$ Hz, so the frequency $f_T$ corresponding to this cardiac frequency is 3 kHz. Because of the circuit involving counter 39 this frequency is retained for precisely 3000 pulses which corresponds to one second. On the other hand, when there is an interval of 0.5 second between two successive cardiac pulses, the cardiac frequency $f_x$ is 2 Hz and the corresponding frequency $f_T$ is 6 kHz. This frequency is maintained 0.5 seconds before adjustable divider 35 is reset, which again corresponds to precisely 3000 pulses. Additional counter 39 also ensures that the average valve formation employed in this example, which is described below, cannot lead to incorrect results.

Since adjustable divider 35 cannot be set to a new division ratio T determined by counter 33 until additional counter 39 releases divider 35 for resetting, storage unit 34 must be designed in such a manner that it can store a plurality of counter readings determined successively by counter 33. When divider 35 is released for resetting, storage unit 34 releases that value which has been stored longest in it.

The type MC 4316L "Programmable modulo-n decade counter" from Motorola, for example, can be employed as the adjustable divider 35. The type TMS 4024 "digital storage buffer (FIFO)" from Texas Instruments, for example, can be employed for the storage unit 34, which is a "first-in, first-out" storage unit. This storage unit stores data at its input when it is supplied with a read command and strobes out stored data when it is supplied with a write command. It is convenient for the write command to be supplied to the FIFO storage unit by counter 39, and for the read command to be supplied by counter 33, which gives the read command, for example, shortly before being set at zero to begin a new count.

From output 38 of adjustable frequency divider 35, frequency $f_T = m f_x$ is supplied to the input of a second pulse shaper 42, which converts the individual pulses, should this be necessary, to pulses having uniform shape and voltage-time area. Connected in series between the output of second pulse shaper 42 and ground is a resistor R1 and a capacitor C1, which form a first integrating network with a time constant $\tau 1 = RC$ of approximately 0.1 second. This first integrating network integrates the pulse train supplied by the output of second pulse shaper 42, which still has a recurrence frequency of $f_T$, so that the voltage at capacitor C1 corresponds to the average value of the pulses supplied by second pulse shaper 42, and is therefore proportional to frequency $f_T$ and thus to the cardiac frequency $f_x$. Since frequency $f_T$ is relatively high, the average value can be formed relatively quickly, so that a time constant $\tau 1$ of approximately 0.1 second is sufficient. With a relative accuracy of approximately $10^{-3}$, the effective voltage at capacitor C1 corresponds to the mathematical average value, and yet the $\tau 1$ value of 0.1 second permits the average value to be able to follow every heartbeat. This means that the voltage thus generated is directly proportional to the instantaneous value of the cardiac frequency.

This instantaneous value can be recorded as a function of time by a recorder, or it can be indicated by a meter. The other characteristic parameters are determined from the instantaneous value with the aid of an analog analyzer 43.

Attached to the connection between resistor R1 and capacitor C1 is the non-inverting input of an operational amplifier V1, with feedback from its output to the inverting input. As is well known, in this circuit the operational amplifier acts as an impedance transformer with a very high input resistance, which does not influence the time constant of the first integrating network, and with a very small output resistance, which permits the connection of numerous other electrical circuits. As shown in FIG. 3, a recorder 45, located in a display 44, and a meter 46 for the instantaneous value of the cardiac frequency are connected at the output of operational amplifier V1. Display 44 has additional meters 47 to 51, which indicate the flutter value, the short-time average value, the short-time drift, the long-time average and the long-time drift.

Also connected to the output of operational amplifier V1 is a flutter-value measuring circuit 55, which will be described in detail below in connection with FIG. 4, and whose output is connected with the flutter-value meter 47. In addition, a second integrating network, comprising a resistor R2 and a capacitor C2 and having a time constant $\tau 2$ which is approximately three hundred times as large as $\tau 1$, is also connected to the output of operational amplifier V1. The second integrating network forms the short-time average value of the cardiac frequency. With the aid of a switch K1, resistor R2 can be bridged by a relatively small resistor R2' in order to reduce the time constant when putting the unit into service, thereby permitting rapid charging of capacitor C2. Switch K1 is then opened again.

In the same manner as described for the first integrating network, the second integrating network is followed by an operational amplifier V2 connected as an impedance transformer. The output of operational amplifier V2 is connected with short-time average-value meter 48, with the input of a short-time drift measuring circuit 60, which will be explained in more detail in connection with FIG. 5, and with the input of a third integrating network, comprising a resistor R3 and a capacitor C3 and having a time constant $\tau 3$ with a value of approximately 10,000 $\tau 1$. In the third integrating circuit this time constant can also be reduced by closing a switch K2, which switches a smaller resistor R3' parallel to resistor R3. The voltage at capacitor C3 corresponds to the long-time average value of the cardiac pulse frequency. Located behind the output of the third integrating network is, again, an impedance transformer comprising an operational amplifier V3 whose output is connected with a long-time average-value meter 50 and with the input of a long-time drift measuring circuit 65 which will be explained in more detail in connection with FIG. 6. Both short-time drift measuring meter 60 and long-time measuring circuit 65 are connected with a control system 70 which supplies control signals S1, S2 and S1', S2' to said circuits and whose significance will be explained below. Short-time drift measuring circuit 60 is connected with short-time drift meter 49, and long-time drift measuring circuit 65 is connected with long-time drift meter 51.

Figure 4:
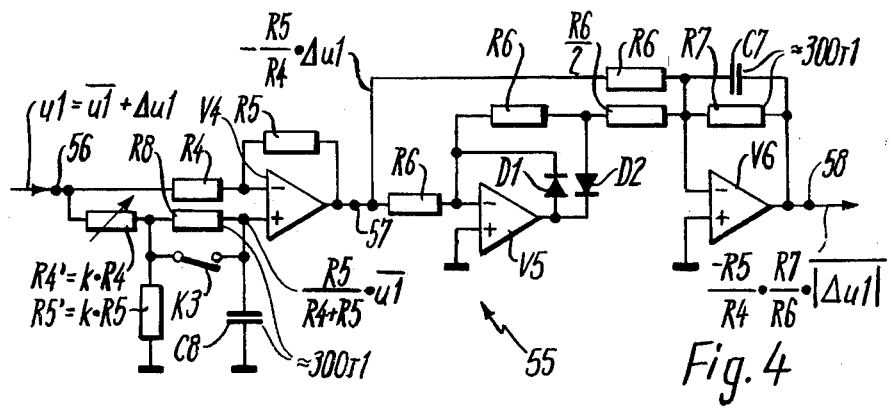
FIG. 4 is a diagram of a circuit for determining the flutter value.

FIG. 4 shows a preferred embodiment of flutter-value measuring circuit 55 shown in FIG. 3. The individual resistors are not designated by different reference symbols, but by their values so that the same designation is employed for resistors of equal size. A voltage ul which is characteristic of the instantaneous value of the cardiac frequency is supplied to the input of the flutter value measuring circuit shown in FIG. 4 from the output of operational amplifier V1 in FIG. 3. This voltage is comprised of a short-time average value $\overline{ul}$ and the differential voltage $\Delta ul$ between the instantaneous value $ul$ and the shorttime average value $\overline{ul}$. To determine the flutter value, it is necessary to eliminate the short-time average value $\overline{ul}$. This is accomplished by means of a differential amplifier, containing an operational amplifier V4, said differential amplifier being designed in such a manner that it amplifies only the differential voltage $\Delta ul$. For this purpose, the inverting input of amplifier V4 is connected with the output of V4 by means of a resistor R5 and with input 56 of the circuit by means of a resistor R4. One end of a variable resistor R4', which can be set to the value $k \cdot R4$, is connected to input 56, while the other end is connected to the non-inverting input of amplifier V4 by means of a resistor R8 and to ground through resistor R5', whose value is $k \cdot R5$. The non-inverting input of amplifier V4 is grounded through a capacitor C8. Resistor R8 and capacitor C8 form an integration network with a time constant of approximately 300 $\tau 1$. A switch K3, which bridges resistor R8, is closed briefly when putting the arrangement into service so that capacitor C8 can be charged as quickly as possible with a voltage which corresponds to the average value $\overline{ul}$. Capacitor C8 can then very quickly accept the voltage corresponding to the precise average value $\overline{ul}$ after switch K3 is opened. As is indicated in FIG. 4, in the steadystate condition there appears across capacitor C8 a voltage equal $$\frac{R5}{(R4+R5)} \cdot \overline{ul},$$

which is proportional to the average value. As a result the voltage at the output of amplifier V4 is proportional to the differential voltage $\Delta ul$. The value of the factor k is selected in such a manner as to provide optimum elimination of average value $\overline{ul}$, which appears as to a common-mode signal amplifier V4. The effective voltage at output 57 of amplifier V4 therefore has a value of $-\Delta ul$ (R5/R4), and represents the instantaneous deviation of voltage ul from average value $\overline{ul}$.

The circuitry following output 57 of amplifier V4 forms the absolute value and an average value with a time constant having a value of approximately 300$\tau 1$. This circuitry has an operational amplifier V5, whose non-inverting input is grounded and whose inverting input is connected with output 57 of operational amplifier V4. Connected to the output of amplifier V5 is the anode of a diode D1, while the cathode is connected with the inverting input. Also connected to the output of amplifier V5 is the cathode of a second diode D2, whose anode is connected with the inverting input through a resistor R6. The inverting input of an operational amplifier V6 is connected with the anode of diode D2 through a resistor having a value of R6/2 and with output 57 of operational amplifier V4 through a resistor R6. The non-inverting input of operational amplifier V6 is grounded, while its output 58 is connected with the inverting input by means of a resistor R7 with a capacitor C7 connected in parallel. If capacitor C7 were not in the circuit, there would be an electrical signal at output 58 which is proportional to the absolute value of that signal present at output 57 of operational amplifier V4. Capacitor C7 is selected so that, together with resistor R7, it provides formation of an average value with a time constant whose value is about 300 $\tau 1$. This therefore compensates for fluctuations in the absolute value of the differential voltage. Thus, a voltage is available at output 58 of operational amplifier V6 whose value is $$-\frac{R5 \cdot R7}{R4 \cdot R6} \cdot \overline{|\Delta ul|}.$$

Output 58 of operational amplifier V6 is connected with flutter-value meter 47, shown in FIG. 3. Through suitable selection of resistors R4, R5, R6 and R7, it is possible for the output signal at point 58 of the circuit to be the desired flutter value, averaged with a time constant of 300$\tau 1$. If desired, the proportionality factor $$\frac{R5 \cdot R7}{R4 \cdot R6}$$

can also be taken into consideration in meter 47.

Figure 4A:
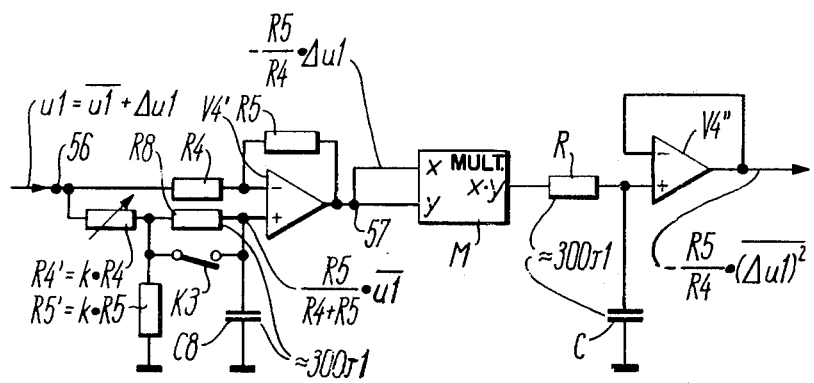
FIG. 4a is a diagram of a circuit for determining the flutter value in which squaring is employed.

As described at the outset, instead of determining the flutter value through formation of the average of the absolute values of the signals present at point 57 of the circuit, it is also possible to square these signals. FIG. 4a shows a circuit suitable for this purpose. Between points 56 and 57 of the circuit, the circuit shown therein coincides with the arrangement shown in FIG. 4. The two inputs $x$ and $y$ of a multiplier M, which supplies a signal at an output $xy$ which is proportional to the product of the signals at the two inputs, are both connected to point 57 of the circuit. The output of multiplier M is connected through a resistor R to a capacitor C and to the non-inverting input of an operational amplifier V which is connected as an impedance transformer. The other connection of capacitor C is grounded. Capacitor C and resistor R forms an integrating network with a time constant of about 300τl.

Since the same input value is supplied to both inputs of multiplier M, the square of the input value is available at the output of the multiplier. Type AD 530 from Analog Devices, Inc., Norwood, Mass. can be employed as the multiplier, for example.

Figure 4B:
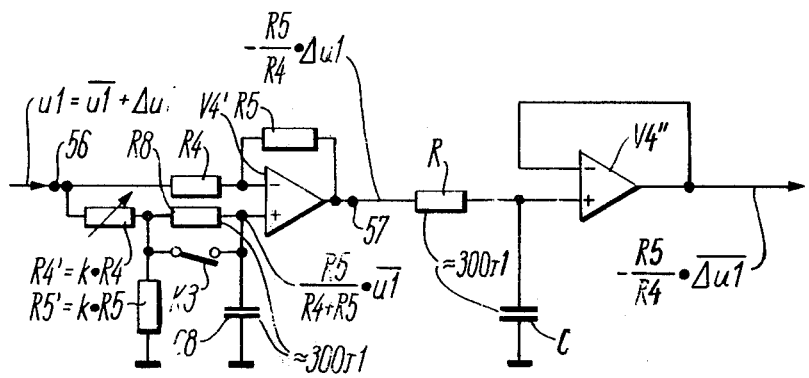
FIG. 4b is a diagram of a circuit for determining the average value of the differences, with correct algebraic signs, between the short-time average value and the instantaneous cardiac pulse frequency.

As explained above, it is possible to determine a flutter value by comparing the instantaneous cardiac pulse frequency with the average value present at the moment, which comes from an earlier time, but it is necessary to take into consideration the influence of a slow change in the average value of the cardiac pulse frequencies on the indication of the flutter value determined in this manner. A circuit suitable for this purpose is shown in FIG. 4b. This circuit determines the differences between the instantaneous cardiac pulse frequency and the shorttime average value and averages them without taking absolute values or squaring. The circuit coincides with FIGS. 4a and 4 between points 56 and 57, differing from the arrangement shown in FIG. 4a only in that there is no multiplier M. Point 57 of the circuit in FIG. 4b is connected directly with resistor R. This arrangement thus forms the average time value of the electrical signals present at point 57 of the circuit.

In measuring the drift values, the first time derivative of the short or long-time average value is, in effect, being sought. However these average values fluctuate only slowly. The commonly used differential circuit comprising an operational amplifier with resistive reverse feedback and capacatative coupling into the inverting input is ordinarily not sufficiently stable to measure these slow drifts reliably. Therefore sample-and-hold circuits are preferred for determining drift values.

Figure 5:
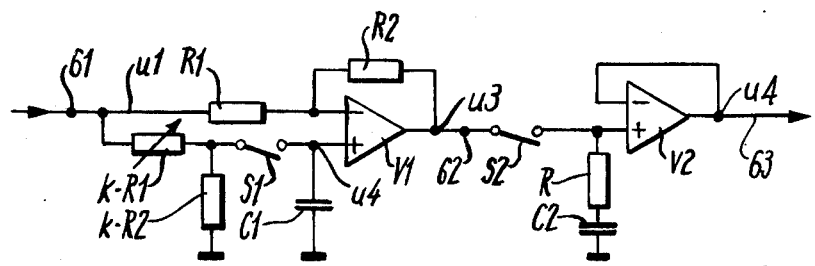
FIG. 5 is a diagram of a circuit for a short-time drift meter.
Figure 6:
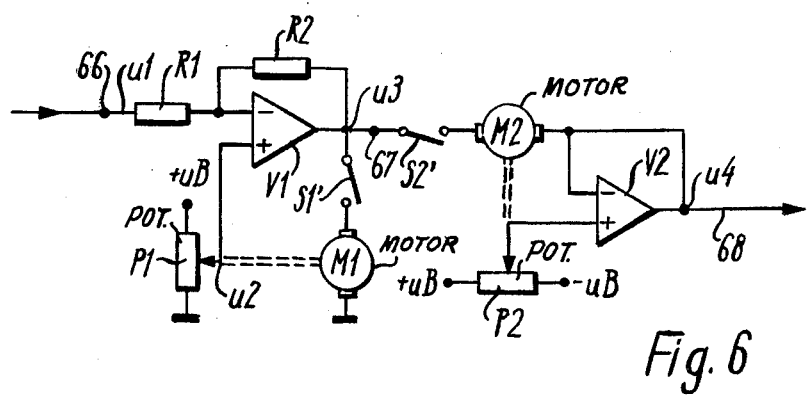
FIG. 6 is a diagram at a circuit for a long-time drift meter.

FIG. 5 shows a preferred embodiment of short-time drift measuring 60 circuit, and FIG. 6 shows a preferred embodiment of long-time drift measuring circuit 65. Since the methods of operation of the arrangements shown in FIGS. 5 and 6 largely coincide, the same designations have been employed wherever possible in both figures, including the voltages. Input voltage ul of the circuit shown in FIG. 5 is the output voltage of amplifier V2 of the circuit shown in FIG. 3, and input voltage ul of the circuit shown in FIG. 6 is the output voltage of operational amplifier V3 of the circuit shown in FIG. 3. The values of resistors R1 and R2 shown in FIGS. 5 and 6 do not necessarily coincide with the resistors R1 and R2 of earlier drawings.

The circuit shown in FIG. 5 comprises two operational amplifiers V1 and V2. Operational amplifier V1 is connected as a differential amplifier in the manner shown in more detail in FIG. 5 and is very similar to the differential amplifier shown in FIG. 4. It differs merely in that it does not contain resistor R8 included in FIG. 4. The switch designated K3 in FIG. 4 is designated S1 in FIG. 5. There is an effective voltage at output 62 of amplifier V1 which corresponds to the difference between input voltage ul, which is supplied at input 61, and the effective voltage at capacitor C1. When switch S1 is open, the effective voltage at capacitor C1 remains unchanged; when switch C1 is closed, the voltage at capacitor C1 is the voltage which is present at the point of connection of resistors k R1 and k R2. Switch S1 and capacitor C1 thus form a sample-and-hold circuit.

A second sample-and-hold circuit is shown in FIG. 5 employing an amplifier V2 and connected to output 62 by means of a switch S2. When switch S2 is closed, the effective voltage at output 62 is sampled by the sample-and-hold circuit formed by amplifier V2 so that, after switch S2 is opened, there is an effective voltage at output 63 of amplifier V2 which corresponds to that voltage which was present at point 62 of the circuit during the closed state of switch S2. If switch S1 is closed, the effective voltage u2 at capacitor C1 changes and assumes a value which is proportional to voltage ul. After switch S1 is opened again, the differential amplifier amplifies the difference resulting from the difference between input voltage ul and the new voltage u2 which is now present at the non-inverting input of amplifier V1. Control of switches S1 and S2 will be explained below in connection with FIG. 7 for the two circuits shown in FIGS. 5 and 6.

Since the holding times required for measuring the longtime drift are very long, the circuit shown in FIG. 6 employs servo-potentiometers for measuring the longtime drift. The servo-potentiometers have a motor which sets a potentiometer as a function of the effective voltage at the motor in such a manner that the effective voltage at the motor assumes a value of zero. Input 66 of the circuit shown in FIG. 6, which is connected with the output of operational amplifier V3 shown in FIG. 3, is connected to the inverting input of an operational amplifier V1 by means of a resistor R1, and the output of the operational amplifier is connected with the inverting input by means of a resistor R2. The slider of a servo-potentiometer formed from a potentiometer P1 and a motor M1 is connected with the non-inverting input of amplifier V1. Potentiomenter P1 is located between a positive voltage $U_B$ and ground. The armature winding of motor M1 is connected between ground and the output of operational amplifier V1 by means of a switch S1'. When switch S1' is open or when voltage u3 at the output of operational amplifier V1 has a value of zero, motor M1 does not move. If there is an effective voltage on the armature winding, motor M1 shifts the slider of potentiometer P1 until voltage u3 reaches a value of zero.

Point 67 of the circuit is connected with the armature winding of a motor M2 by means of a second switch S2', motor M2 belonging to a second servo-potentiometer. The other armature connection of the armature winding of motor M2 is connected with both the inverting input and the output of an operational amplifier V2. The non-inverting input of operational amplifier V2 is connected with the slider driven by motor M2 of a potentiometer P2, whose other connections are connected between a positive and a negative operating voltage. Motor M2 does not move when switch S2' is open or if the effective voltage at armature winding of motor M2 has a value of zero. If this voltage does not have a value of zero, the slider of potentiometer P2 is shifted until this voltage assumes a value of zero.

Figure 7:
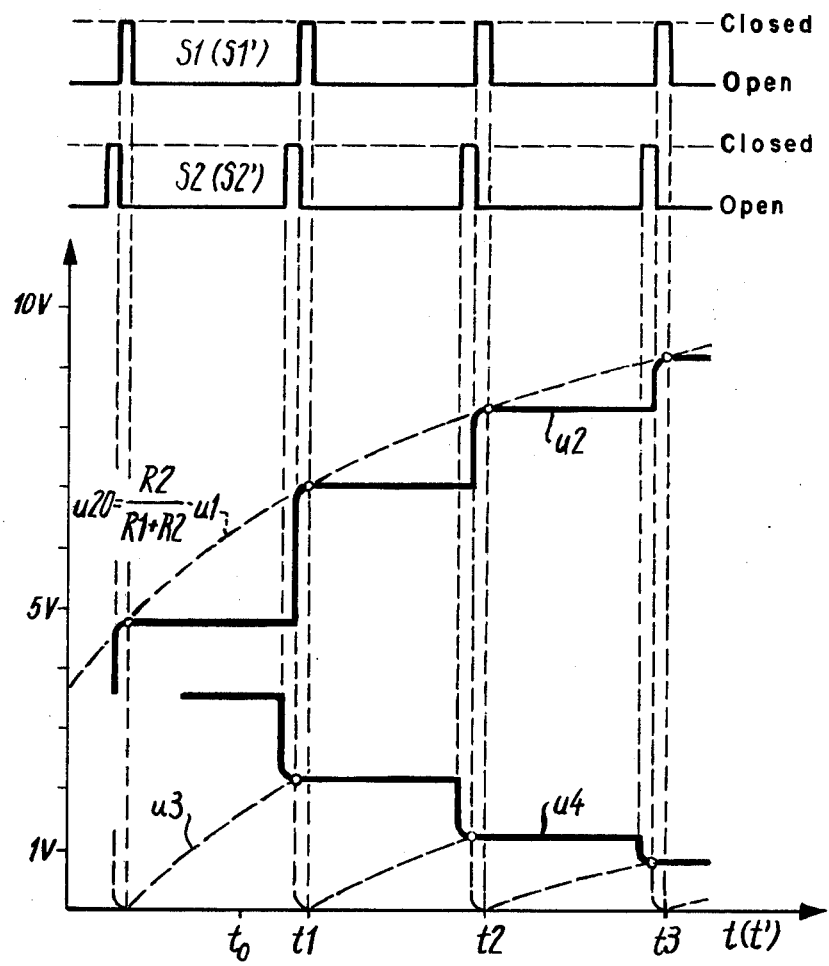
FIG. 7 is a timing diagram for explaining the circuits illustrated in FIGS. 5 and 6.

The method of operation of the circuits described in FIGS. 5 and 6 will now be explained by referring to the timing diagram shown in FIG. 7. At the top, FIG. 7 shows at which times switches S1 and S2 of the circuit of FIG. 5 are closed and open. The time in which switch S1 and switch S2 are open is approximately 5 to 30 seconds, for example. The time in which switches S1' and S2' are open amount to approximately 3 to 15 minutes, as desired.

The fact that the curves shown in FIG. 7 are valid for two different time scales is indicated by the fact that the time axis is designated "$t\ (t')$".

The curve for the voltage $$u20 = \frac{R2}{R1 + R2}.$$

ul was drawn on FIG. 7 in the form of a dashed line for an assumed characteristic of input voltage ul, which itself is not shown in FIG. 7. Voltage u20 is that voltage which must be present at the non-inverting input of amplifier V1 of the arrangement shown in FIG. 5 and in FIG. 6 in order for voltage u3 at output 62 (FIG. 5) or 67 (FIG. 6) of amplifier V1 to have a value of zero at a given voltage ul. However with a changing voltage ul, voltage u2 generally does not have the value u20, since S1 (FIG. 5) is generally open and therefore the voltage at the non-inverting input of amplifier V1 cannot follow voltage u20. Switch S1' (FIG. 6) is also open most of the time, so that motor M1 of potentiometer P1 cannot adjust in such a manner that voltage u2 assumes the value u20. If voltage u2 does not have the value u20, voltage u3 differs from zero.

As an example at a time to, voltage u2 has a value of 4.7V in accordance with the arbitrarily indicated voltage scale in FIG. 7. At time t1, switch S2 (S2') is first briefly closed, so that in the circuit FIG. 5 capacitor C2 can charge to that value of voltage u3 which is present at that moment at point 62 in the circuit. In the circuit shown in FIG. 6, at time t1, when switch S2' is closed, motor M2 starts and shifts potentiometer P2 until voltage u4 assumes the value of voltage u3 at point 67 of the circuit. After switch S2 or S2' has been opened again, switch S1 or S1' is briefly closed to enable voltage u2 to assume the value u20. In the circuit shown in FIG. 5, this is accomplished since capacitor C1 charges to voltage u2 = u20; in the circuit of FIG. 6, this occurs in that motor M1 shifts potentiometer P1 until voltage u2 has assumed the value u20, thereby stopping motor M1. When voltage u2 has been set equal to u20, voltage u3 has a value of zero. As input voltage ul supplied to input 61 (FIG. 5) or 66 (FIG. 6) increases further, a voltage u3 appears at point 62 or 67 of the circuit corresponding to the difference between input voltage ul and the effective voltage u2 at the non-inverting input of amplifier V1. In FIG. 7, it can be seen that voltage u3 increases again from time t1 on. At time t2 the value of voltage u3 present is first sampled by the second sample-and-hold circuit shown in FIGS. 5 and 6, by closing switches S2 and S2' and is provided at outputs 63 and 68 as voltage u4. By closing switch S1 and S1', voltage u3 is then reduced to zero by matching voltage u2 to voltage u20. The voltage jump performed by voltage u2 at the individual times $t1, t2, t3$ thus results in a voltage u4 directly subsequent to these times, said voltage u4 being proportional to the above-mentioned voltage jumps and, with suitable values for the components making up the circuits shown in FIGS. 5 and 6, being just as large as the change in input voltage ul between times $t1$ and $t2, t2$ and $t3$, and so forth.

The magnitude of voltage u4 of the circuit shown in FIG. 5 therefore corresponds to the short-time drift, which is the drift of the short-time average value of the cardiac frequency within the periods located between times $t1, t2, t3$, and so forth. Voltage u4 of the circuit shown in FIG. 6 corresponds to the long-time drift within the corresponding periods.

The time control of switches S1, S2, S1' and S2' described here is performed by means of the control system 70 depicted in FIG. 3.

It may be desirable to record not only the instantaneous cardiac pulse frequency with a recorder, as is shown in FIG. 3, but also to record other values determined by the present invention. In this regard it may also be desirable to employ recorders which can be record for extended periods of time such as 24 hour recorders. It is possible to employ recorders for this application which are similar to those employed as trip recorders in motor vehicles. Recorders which record for extended periods of time simplify and aid the statistical analysis of the values determined by the present invention.

As will be obvious to those skilled in the art, numerous modifications may be made to the preferred embodiments described and illustrated herein without departing from the invention as defined in the claims.

I claim:

1. An apparatus for examining the cardiacpulse frequency comprising:
   a. an input for accepting a cardiac-pulse signal;
   b. a pulse shaper and means connecting the pulse shaper to said input;
   c. a pulse generator capable of producing a train of pulses with a recurrence frequency which is greater than the cardiac-pulse frequency;
   d. a gate and means connecting said pulse generator to an input of the gate;
   e. a first control unit for enabling said gate during a period of time between two cardiac-pulses, the pulses being separated by at most only a few intervening cardiac-pulses, means connecting said pulse shaper to the first control unit, and means connecting the first control unit to said gate;
   f. a first counter and means connecting an output of said gate to the first counter;
   g. computing means for computing parameters relating to the cardiac-pulse frequency; the parameters comprising an instantaneous cardiac-pulse frequency and a frequency flutter value; and means connecting an output of the first counter to the computing means; and
   h. display means for displaying parameters comprising the parameters listed in (g) and means connecting the computing means to the display means.

2. The apparatus according to claim 1 in which the parameters relating to the cardiac-pulse frequency further comprise a short-time average cardiac-pulse frequency.

3. The apparatus according to claim 2 in which the computing means comprise a second control unit and a digital arithmetic unit.

4. The apparatus according to claim 2 in which the means connecting the pulse generator to an input of the gate comprises:
- d.1 a first frequency divider having a predetermined divisional factor, the divisional factor being selected so that a frequency of the signal at an output of the first frequency divider is substantially lower than the recurrence frequency of the train of pulses of said pulse generator and substantially greater than the cardiac pulse frequency,
- d.2 means connecting an output of said pulse generator with an input of the first frequency divider, and
- d.3 means connecting an output of the first frequency divider to the input of the gate; and the computing means comprising:
- g.1 a second frequency divider having an adjustable divisional factor which may be set to the reciprocal of a selected number and means for setting the divider to a predetermined initial value, means connecting an output of said pulse generator to an input of the second frequency divider, and means for setting the adjustable divisional factor equal to the reciprocal of a number at an output of said first counter,
- g.2 a second counter, means connecting an input of the counter to an output of said second frequency divider, and means connecting an output of the second counter to the means of the second frequency divider for setting the divider to a predetermined initial value,
- g.3 a first integrating network for generating a signal substantially proportional to an instantaneous cardiac-pulse frequency characterized by an integration time constant of no greater than approximately the period of time between two cardiac pulses, the pulses being separated by at most only a few intervening cardiac pulses, and means connecting an output of the second frequency divider to an input of the first integrating network,
- g.4 a second integrating network for generating a signal substantially proportional to a short-time average cardiac-pulse frequency characterized by an integration time constant substantially greater than the time constant of the first integrating network, and means connecting an output of the first integrating network to an input of the second integrating network, and
- g.5 a frequency flutter-value measuring circuit for producing a signal related to the difference between the instantaneous cardiac-pulse frequency and a short-time average value of the cardiac-pulse frequency comprising a differential amplifier having an inverting input and non-inverting input, means connecting an outut of the first integrating network to one input of the differential amplifier, and means for applying a short-time average value of a signal at an output of the first integrating network to another input of the differential amplifier.

5. An apparatus for examining the cardiac pulse frequency comprising:
- a. an input for accepting a cardiac pulse signal
- b. a pulse shaper and means connecting the pulse shaper to said input,
- c. a pulse generator capable of producing a train of pulses with a recurrence frequency which is greater than the cardiac pulse frequency,
- d. a gate and means connecting said pulse generator to an input of the gate,
- e. a first control unit for enabling said gate during a period of time between two cardiac pulses, the pulses being separated by at most only a few intervening cardiac pulses, means connecting said pulse shaper to the first control unit, and means connecting the first control unit to said gate,
- f. a counter and means connecting an output of said gate to the counter,
- g. computing means for computing parameters relating to the cardiac pulse frequency; the parameters comprising an instantaneous cardiac-pulse frequency, a short-time average cardiac-pulse frequency and a frequency flutter value; the computing means comprising a second control unit and a digital arithmetic unit and means connecting an output of said counter to the arithmetic unit,
- h. storage registers for storing parameters comprising the parameters listed in (g) and means connecting the arithmetic unit to the storage registers, and
- i. display means for displaying parameters stored in said storage registers and means connecting said storage registers to the display means.

6. The apparatus according to claim 5 in which the parameters relating to the cardiac pulse frequency further comprise a drift of the short-time average frequency, and the apparatus further comprises a display means for displaying the parameter measuring the drift of the short-time average frequency, a storage register for storing the short-time drift parameter, means connecting the display means to the storage register, and means connecting the storage register to the arithmetic unit.

7. The apparatus according to claim 5 in which the parameters relating to the cardiac-pulse frequency further comprise a long-time average frequency, and the apparatus further comprises a display means for displaying the long-time average frequency, a storage register for storing the long-time average frequency, means connecting the display means to the storage register, and means connecting the storage register to the arithmetic unit.

8. The apparatus according to claim 7 in which the parameters relating to the cardiac pulse frequency further comprise a drift of the long-time average frequency, and the apparatus further comprises a display means for displaying the parameter measuring the drift of the long-time average frequency, a storage register for storing the long-time drift parameter, means connecting the display means to the storage register, and means connecting the storage register to the arithmetic unit.

9. The apparatus according to claim 5 in which the parameters relating to the cardiac pulse frequency further comprise a differential frequency flutter value, and the apparatus further comprises a display means for displaying the differential frequency flutter value, a storage register for storing the differential frequency value, means connecting the display means to the storage register, and means connecting the storage register to the arithmetic unit.

10. An apparatus for examining the cardiac pulse frequency comprising:
- a. an input for accepting a cardiac pulse signal,
- b. a pulse shaper and means connecting the pulse shaper to said input,
- c. a pulse generator capable of producing a train of pulses with a recurrence frequency which is substantially greater than the cardiac pulse frequency, d. a first frequency divider having a predetermined divisional factor and means connecting an output of said pulse generator with an input of the first frequency divider, the divisional factor being selected so that a frequency of the signal at an output of the first frequency divider is substantially lower than the recurrence frequency of the train of pulses of said pulse generator and substantially greater than the cardiac pulse frequency, e. a gate and means connecting an output of said first frequency divider to an input of the gate, f. a control unit for enabling said gate during a period of time between two cardiac pulses, the pulses being separated by at most only a few intervening cardiac pulses, means connecting said pulse shaper to the control unit, and means connecting the control unit to said gate, g. a first counter and means connecting an output of said gate to the counter, h. a second frequency divider having an adjustable divisional factor which may be set to the reciprocal of a selected number and means for setting the divider to a predetermined initial value, means connecting an output of said pulse generator to an input of the second frequency divider, and means for setting the adjustable divisional factor equal to the reciprocal of a number at an output of said first counter, i. a second counter, means connecting an input of the counter to an output of said second frequency divider, and means connecting an output of the second counter to the means of the second frequency divider for setting the divider to a predetermined initial value, j. a first integrating network for generating a signal substantially proportional to an instantaneous cardiac-pulse frequency characterized by an integration time constant of no greater than approximately the period of time between two cardiac pulses, the pulses being separated by at most only a few intervening cardiac pulses, and means connecting an output of the second frequency divider to an input of the first integrating network, k. a first display means for displaying an instantaneous cardiac pulse frequency and means connecting an output of the first integrating network to an input of the first display means, l. a second integrating network for generating a signal substantially proportional to a short-time average cardiac-pulse frequency characterized by an integration time constant substantially greater than the time constant of the first integrating network, means connecting an output of the first integrating network to an input of the second integrating network, and switching means for reducing the time constant to a shorter value, m. a second display means for displaying a short-time average cardiac-pulse frequency and means connecting an output of the second integrating network to an input of the second display means, n. a frequency flutter-value measuring circuit for producing a signal related to the difference between the instantaneous cardiac pulse frequency and a short-time average value of the cardiac pulse frequency comprising a differential amplifier having an inverting input and non-inverting input, means connecting an output of the first integrating network to one input of the differential amplifier, and means for applying a shorttime average value of a signal at an output of the first integrating network to another input of the differential amplifier, and o. a third display means for displaying the frequency flutter-value and means connecting an output of the frequency flutter-value measuring circuit to the third display means.

11. The apparatus according to claim 10 in which the frequency flutter-value measuring circuit further comprises:

n.1 a diode circuit connected to an output of the differential amplifier for producing a signal substantially proportional to the absolute value of the difference between the instantaneous cardiac pulse frequency and the short-time average value of the cardiac pulse frequency applied to the differential amplifier, and n.2 a third integrating network connected to an output of the diode circuit for producing an average value of the absolute-value signal.

12. The apparatus according to claim 10 in which the frequency flutter-value measuring circuit further comprises:

n.1 a multiplier circuit connected to an output of the differential amplifier for producing a signal substantially proportional to the square of the difference between the instantaneous cardiac pulse frequency and the short-time average value of the cardiac pulse frequency applied to the differential amplifier, and n.2 a third integrating network connected to an output of the multiplier circuit for producing an average value of the squared signal.

13. The apparatus according to claim 10 further comprising means for measuring the drift of an average frequency.

14. The apparatus according to claim 13 in which the means for measuring the drift of an average frequency includes:

p. a first sample-and-hold means for sampling a signal substantially proportional to an average frequency at first predetermined times and storing the sampled signal;

q. means connecting an input of the first sample-and-hold means to an output of an integrating circuit for producing the average-frequency signal;

r. a second differential amplifier having an inverting input and a noninverting input, means connecting one input of the second differential amplifier to an output of the first sample-and-hold means, and means connecting the other input of the second differential amplifier to the output of the integrating circuit;

s. a second sample-and-hold means connected to an output of the second differential amplifier for sampling at second predetermined times a signal at the output and storing the sampled signal, the sampled signal being substantially proportional to the difference between the average-frequency signal at one of the second predetermined times and at a corresponding earlier first predetermined time; and t. a control circuit for generating timing signals at the first and second predetermined times and means connecting the control circuit to the first and second sample-and-hold circuits so that timing signals at the first predetermined times are transmitted to the first sample-and-hold circuit and timing signals at the second predetermined times are transmitted to the second sample-and-hold circuit.

15. The apparatus according to claim 14 in which the integrating circuit connected to the first sample-and-hold means is the second integrating network so that the means for measuring the drift measures the drift in the short-time average cardiac-pulse frequency.

16. The apparatus according to claim 14 in which the first and second sample-and-hold means each include a capacitor connected to a switch.

17. The apparatus according to claim 14 in which the first and second sample-and-hold means each include a potentiometer driven by a motor.

* * * * *

UNITED STATES PATENT AND TRADEMARK OFFICE
CERTIFICATE OF CORRECTION

PATENT NO. : 4,022,192
DATED : May 10, 1977
INVENTOR(S) : Günther R. Laukien

It is certified that error appears in the above-identified patent and that said Letters Patent are hereby corrected as shown below:

Column 5, line 68, "of time b" should read --at time b--.

Column 7, line 9, "instantaneousvalue" should read --instantaneous value--.

Column 7, line 26 "-m" should read --=m--.

Column 8, line 10, "$\tau + \frac{T}{1}$" should read --$\tau + \frac{T}{2}$--

Column 8, line 22, "$\tau + \frac{T}{1}$" should read --$\tau + \frac{T}{2}$--

Column 14, line 8, "equal" should read --equal to--.

Column 16, line 47, "Potentiomenter" should read --Potentiometer--.

Column 19, line 54, "an outut of" should read --an output of--.

Signed and Sealed this twenty-third Day of August 1977

[SEAL]

Attest:

RUTH C. MASON
Attesting Officer

C. MARSHALL DANN
Commissioner of Patents and Trademarks